(12) United States Patent
Ford et al.

(10) Patent No.: US 10,112,904 B2
(45) Date of Patent: Oct. 30, 2018

(54) PROCESS FOR PREPARING SYNTHETIC INTERMEDIATES FOR PREPARING TETRAHYDROQUINOLINE DERIVATIVES

(71) Applicant: DEZIMA PHARMA B.V., Thousand Oaks, CA (US)

(72) Inventors: John Ford, Cambridgeshire (GB); Johannes Paulus Gerardus Seerden, MC Gronningen (NL); Amandine Ledru, Belfast (GB)

(73) Assignee: DEZIMA PHARMA B.V., Naarden (NL)

( * ) Notice: Subject to any disclaimer, the term of this patent is extended or adjusted under 35 U.S.C. 154(b) by 0 days.

(21) Appl. No.: 15/503,686

(22) PCT Filed: Jul. 29, 2015

(86) PCT No.: PCT/NL2015/050555
§ 371 (c)(1),
(2) Date: Feb. 13, 2017

(87) PCT Pub. No.: WO2016/024858
PCT Pub. Date: Feb. 18, 2016

(65) Prior Publication Data
US 2017/0267640 A1   Sep. 21, 2017

(30) Foreign Application Priority Data

Aug. 12, 2014 (NL) .................. PCT/NL2014/050556

(51) Int. Cl.
C07D 401/12       (2006.01)
C07D 215/42       (2006.01)

(52) U.S. Cl.
CPC ......... *C07D 215/42* (2013.01); *C07D 401/12* (2013.01)

(58) Field of Classification Search
CPC ............................ C07D 215/42; C07D 401/12
USPC .......................... 544/298, 330, 331; 546/159
See application file for complete search history.

(56) References Cited

FOREIGN PATENT DOCUMENTS

WO    2000/0017164 A1   3/2000
WO    2007/116922 A1    10/2007

OTHER PUBLICATIONS

Am Ende DJ. et al.; A Calorimetric Investigation to Safely Scale-Up a Curtius Rearrangement of Acryloyl Azide; Org Proc Res Dev. 1998;2:382-392.
Baigent, C. et al.; Cholesterol Treatment Trialists (CTT) Collaboration. Efficacy and safety of more intensive lowering of LDL cholesterol: a meta-analysis of data from 170000 participants in 26 randomized trials. Lancet. 2010; 13: 1670-1681.
Barter PJ, et al.; Effects of Torcetrapib in patients at high risk for coronary events. N Engl J Med. 2007; 357: 21009-2122.
Barter PJ, et al.; Relationship between atorvastatin dose and the harm caused by torcetrapib. J Lipid Res. 2012; 53: 2436-2442.
Bloomfield D. et al., Efficacy and safety of the cholesteryl ester transfer protein inhibitor anacetrapib as monotherapy and coadministered with atorvastatin in dyslipidemic patients. Am Heart J. 2009;157 352-360.
Dagousset G. et al; Chiral Phosphoric Acid-Catalyzed Enantioselective Three-Component Povarov Reaction Using Enecarbamates as Dienophiles: Highly Diastereo- and Enantioselective Synthesis of Substituted 4-Aminotetrahydroquinolines. J Am Chem Soc. 2011;133 14804-14813.
Damon DB et al.; Synthesis of the CETP Inhibitor Torcetrapib: The Resolution Route and Origin of Stereoselectivity in the Iminium Ion Cyclization. Org Proc Res Dev. 2006;10: 464-471.
Di Angelantonio, Emanuele, MD. et al.; The Emerging Risk Factors Collaboration. Major lipids, apolipoproteins, and risk of vascular disease. JAMA. 2009; 302: 1993-2000.
Escribano, Ana et al.; Design and synthesis of new tetrahydroquinolines derivatives as CETP inhibitors; Bioorganic & Medicinal Chemistry Letters, Pergamon, Amsterdam, NL, vol. 22, No. 11, Apr. 7, 2012; pp. 3671-3675.
Escribano, Ana et al.; Design and Synthesis of New Tetrahydroquinolines Derivatives as CETP Inhibitors; XP002730O88, retrieved from STN Database accession No. 2012:630964, abstract.
Forrest MJ. et al.; Torcetrapib-induced blood pressure elevation is independent of CETP inhibition and is accompanied by increasing circulating levels of aldosterone. Br J Pharmacol. 2008;154: 1465-1473.
Gotto, Antonio M. Jr. et al.; Evaluation of Lipids, Drug Concentration, and Safety Parameters Following Cessation of Treatment With the Cholesteryl Ester Transfer Protein Inhibitor Anacetrapib in Patients With or at High Risk for Coronary Heart Disease; Am. J. Cardiol., 2014;113(1):76-83.
Govindan CK; An improved process for the preparation of benzyl-N-vinyl carbamate . Org Proc Res Dev. 2002;6:74-77.
Huang D. et al.; Highly enantioselective three-component Povarov reaction catalyzed by SPINOL-phosphoric acids. RSC Advances. 2013; 3: 573-578.
Kastelein JJP, et al. Effect of torcetrapib on carotid atherosclerosis in familial hypercholesterolemia. N Engl J Med. 2007;356: 1620-1630.
Kouznetsov et al.; Recent synthetic developments in a powerful imino Diels-Alder reaction (Povarov reaction): application to the synthesis of N-polyheterocycles and related alkaloids, Tetrahedron, Elsevier Science Publishers, Amsterdam, NL; vol. 65, No. 14, 2009; 2721-2750.

(Continued)

*Primary Examiner* — Deepak R Rao
(74) *Attorney, Agent, or Firm* — Elsa D. Lemoine

(57) ABSTRACT

The present invention relates to a process for the preparation of synthetic intermediates which may be used in the preparation of tetrahydroquinoline derivatives, which derivatives have an inhibitory activity against cholesteryl transfer protein (CETP), show effects of increasing HDL cholesterol level and decreasing LDL cholesterol level, and can be used for the treatment and/or prevention of diseases such as arteriosclerotic diseases, hyperlipidemia, dyslipidemia and the like.

15 Claims, No Drawings

(56) References Cited

OTHER PUBLICATIONS

Krishna R, et al. Multiple-dose pharmacodynamics and pharmacokinetics of anacetrapib, a potent cholesteryl ester transfer protein (CETP) inhibitor, in healthy subjects. Clin Pharmacol Ther. 2008;84: 679-683.

Liu H. et al. Chiral Bronsted Acid-Catalyzed Enantioselective Three-Component Povarov Reaction. J Am Chem Soc. 2009; 131: 4598-4599.

Luscher TF, et al. Vascular effects and safety of dalcetrapib in patients with or at risk of coronary heart disease: the dal-VESSEL randomized clinical trial. Eur Heart J.; 2012;33: 857-865.

Nicholls SJ, et al.; Cholesteryl ester transfer protein inhibition, high-density lipoprotein raising, and progression of coronary atherosclerosis. Insights from ILLUSTRATE (Investigation of Lipid Level Management Using Coronary Ultrasound to Assess Reduction of Atherosclerosis by CETP Inhibition and HDL Elevation). Circulation. 2008; 118: 2506-2514.

Nicholls SJ, et al.; Effects of the CETP inhibitor evacetrapib administered as monotherapy or in combination with statins on HDL and LDL cholesterol. JAMA. 2011;306: 2099-2109.

Roger VL, et al.; Heart disease and stroke statistics—2012 Update: A report from the American Heart Association. Circulation. 2012;125: e012-e230.

Simic B., et al.; Torcetrapib impairs endothelial function in hypertension. Eur Heart J. 2012;33 1615-1624.

Schwartz GG. et al.; Effects of dalcetrapib in patients with recent acute coronary syndrome. N Engl J Med. 2012; 367:22: 2089-2099.

Stein EA, et al.; Safety and tolerability of dalcetrapib. Am J Cardiol. 2009;104: 82-91.

Vergeer M, et al.; Cholesteryl ester transfer protein inhibitor torcetrapib and off-target toxicity: pooled analysis of the rating atherosclerotic disease change by imaging with a new CETP inhibitor (RADIANCE) trials. Circulation. 2008;118: 2515-2522.

PROCESS FOR PREPARING SYNTHETIC INTERMEDIATES FOR PREPARING TETRAHYDROQUINOLINE DERIVATIVES

CROSS REFERENCES TO RELATED APPLICATIONS

This application is a National Stage Application under 35 U.S.C. § 371 of International Application No. PCT/NL2015/050555, having an international filing date of Jul. 29, 2015, which is claiming priority from an International Application No. PCT/NL2015/050556, having an international filing date of Aug. 12, 2014.

TECHNICAL FIELD OF THE INVENTION

The present invention relates to a process for the preparation of synthetic intermediates which may be used in the preparation of tetrahydroquinoline derivatives, which derivatives have an inhibitory activity against cholesteryl transfer protein (CETP), show effects of increasing HDL cholesterol level and decreasing LDL cholesterol level, and can be used for the treatment and/or prevention of diseases such as arteriosclerotic diseases, hyperlipidemia, dyslipidemia and the like.

BACKGROUND OF THE INVENTION

Prospective epidemiological studies have shown a strong association between low density lipoprotein-cholesterol (LDL-C) levels and cardiovascular disease (CVD) risk [1]. The subsequent application of statin therapy to decrease these atherogenic LDL-C levels has resulted in a marked reduction of CVD-related morbidity and mortality: every 1 mmol/L decrease in LDL-C results in an estimated 22% reduction of CVD events and a 10% reduction of all-cause mortality [2]. Notwithstanding these impressive benefits, a large residual disease burden persists that has a large impact on both individual patients as well as on global healthcare costs [3]. Novel therapeutics are required to reduce further this residual CVD risk in patients.

One new approach which reduces LDL-C and elevates high-density lipoprotein cholesterol (HDL-C) levels is to inhibit Cholesterol Ester Transfer Protein (CETP). CETP is a plasma protein secreted primarily by liver and adipose tissue. CETP mediates the transfer of cholesteryl esters from HDL to apolipoprotein B (Apo B)-containing particles (mainly LDL and very low density lipoprotein VLDL) in exchange for triglycerides, thereby decreasing the cholesterol content in HDL in favor of that in (V)LDL. Hence, CETP inhibition has been hypothesized to retain cholesteryl esters in HDL-C and decrease the cholesterol content of the atherogenic Apo B fraction.

Despite the evidence supporting the potential of CETP inhibition in reducing cardiovascular morbidity, clinical development of CETP inhibitors has not been straightforward. The first compound to progress to phase III clinical trials was torcetrapib which, although it showed efficacy, was withdrawn from development owing to safety concerns including an unexpected increase in cardiovascular events and death when in combination with atorvastatin, compared with atorvastatin alone [4].

Another CETP inhibitor, dalcetrapib, which entered phase IIb clinical trials was shown to be a weak inhibitor that increased HDL-C by 30-40% with minimal effects on LDL-C concentrations but did not appear to exhibit the off-target effects of torcetrapib [11-13]. Recently, dalcetrapib development has also been terminated on the grounds of futility in a phase III study which was carried out with this compound.

Two more CETP inhibitors, anacetrapib and evacetrapib, are currently in phase III clinical trials. However, a disadvantage of the use of these CETP-inhibitors is that due to the relatively high dosage which has to be used to obtain CETP-inhibition, more and stronger side effects may occur. This can have a negative influence on both the physical well-being of the patient as well as on patient compliance.

Current inventors successfully overcame the above mentioned disadvantages by providing a potent and well tolerated CETP-inhibitor and a pharmaceutical composition thereof. This CETP-inhibitor is the tetrahydroquinoline derivative referred to as Compound A and has the following structural formula:

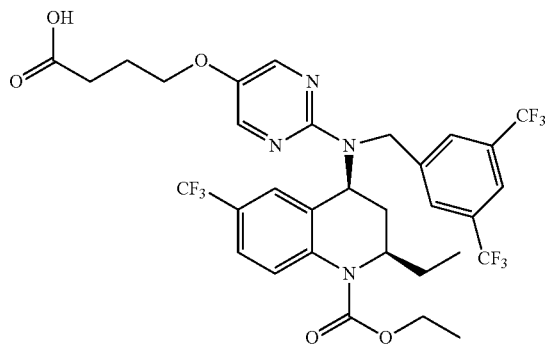 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

Clinical studies have shown that Compound A (or a salt thereof) is a potent CETP-inhibitor. Compared to other known CETP-inhibitors, only a relatively low dose of Compound A is needed to reach near complete CETP inhibition. Typically, repeated once daily dosages as low as 2.5 mg of Compound A have proven to be already sufficient to reach near complete CETP-inhibition. These are considerably lower dosages than had to be used for other CETP-inhibitors. Moreover, clinical studies have also shown that Compound A is well tolerated and that it does not lead to serious side effects.

For the preparation of tetrahydroquinoline derivatives, such as Compound A, use has been made of the intermediates according to formula I

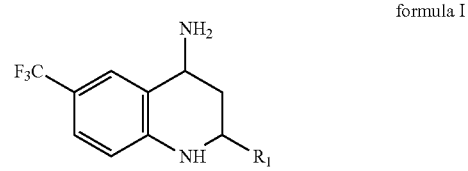

formula I

Although these kinds of intermediates are very useful in the preparation of tetrahydroquinoline derivatives, such as Compound A, with the current methods for preparing these kinds intermediates, such as described in WO2007/116922, the overall yield is relatively low. Moreover relatively expensive starting materials and catalysts have to be used, such as (R)-3-aminovaleric acid and palladium, respectively. Furthermore, in the current methods of manufacturing problems arise with residual fluorine corroding manufacturing equipment.

Hence, a need exists for an efficient and cost effective process for preparing intermediates according to formula I, which may be used in the further preparation of tetrahydroquinoline derivatives having CETP inhibiting properties, such as Compound A.

SUMMARY OF THE INVENTION

A first aspect of the present invention relates to a process for preparing the compound of formula I or a salt thereof:

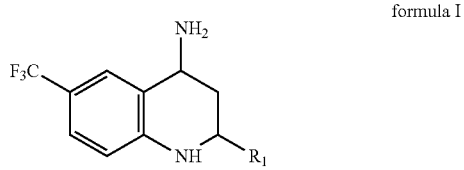

formula I comprising the steps of:
(a) reacting 4-aminobenzotrifluoride according to formula II

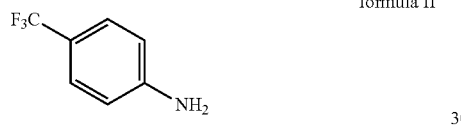

formula II with an aldehyde according to formula III

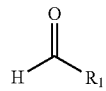

formula III and with a compound according to formula IV

formula IV in the presence of a solvent and optionally one or more catalysts to form the compound of formula V

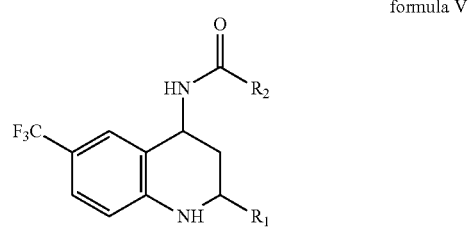

formula V wherein
$R_1$ is H or $C_1$-$C_3$ alkyl, preferably $CH_2CH_3$;
$R_2$ is H, $C_1$-$C_3$ alkyl or

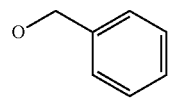

(b) hydrolyzing the compound of formula V to form the compound of formula I.

With the process of the present invention it is now possible to prepare efficiently, with relatively cheap starting materials, with few byproducts and with a good yield the intermediate compounds according to formula I. As mentioned above, these compounds may be used in the further preparation of tetrahydroquinoline derivatives, such as Compound A.

In the process according to the present invention, use is made of a so-called three component Povarov reaction. A key step in this process is the formation of the so-called Povarov product according to formula V:

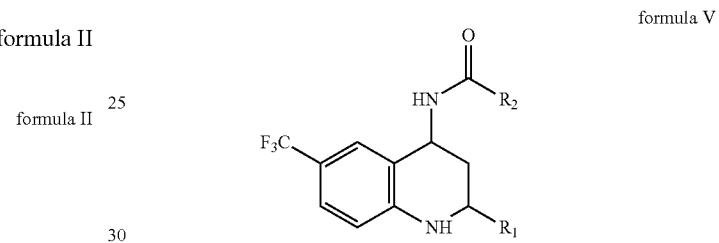

formula V

This intermediate may be prepared with relatively cheap starting materials and may efficiently be hydrolyzed to form the compound according to formula I.

Hence, a second aspect of the present invention relates to the intermediate according to formula V as such as this intermediate has not been prepared before.

A third aspect of the present invention relates to the use of the intermediate according to formula V in the preparation of a compound according to formula I, in particular in the preparation of the 2R,4S enantiomers thereof according to formula I-a, which enantiomers may be used in the preparation of Compound A.

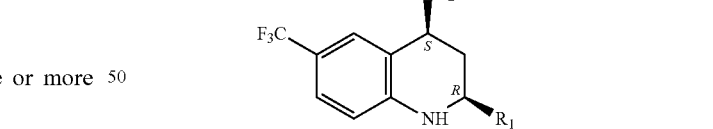

formula I-a

Hence, a last aspect of the present invention relates to the use of the compound according to formula V in the preparation of Compound A.

Definitions

The term 'pharmaceutically acceptable' as used herein has its conventional meaning and refers to compounds, material, compositions and/or dosage forms, which are, within the scope of sound medical judgment suitable for contact with the tissues of mammals, especially humans, without excessive toxicity, irritation, allergic response and other problem complications commensurate with a reasonable benefit/risk ratio.

The term 'salt' as used herein has its conventional meaning and includes the acid addition and base salts.

The term 'treatment' as used herein has its conventional meaning and refers to curative, palliative and prophylactic treatment.

The term 'cardiovascular disease' has its conventional meaning and includes arteriosclerosis, peripheral vascular disease, hyperlipidemia, mixed dyslipidemia betalipoproteinemia, hypoalphalipoproteinemia, hypercholesteremia, hypertriglyceridemia, familial-hypercholesteremia, angina, ischemia, cardiac ischemia, stroke, myocardial infarction, reperfusion injury, restenosis after angioplasty, hypertension, cerebral infarction and cerebral stroke.

The term "halo", "halogen atom" or "halogen" refers to fluorine, chlorine, bromine or iodine.

The term "alkyl" or "alkyl group" as used herein has its conventional meaning and refers to a straight or branched saturated hydrocarbon chain having 1 to 10 carbon atoms and a cyclic saturated hydrocarbon chain having 3 to 10 carbon atoms.

The term "$C_1$-$C_3$ alkyl" as used herein has its conventional meaning and refers to an alkyl group having 1 to 3 carbon atoms. Examples of such alkyl groups are methyl, ethyl, propyl and isopropyl.

DETAILED DESCRIPTION OF THE INVENTION

A process for the preparation of tetrahydroquinoline derivatives has been described in WO 2007/116922. Although tetrahydroquinoline derivatives, such as Compound A, may be prepared with the above mentioned process, this process was low-yielding and generated a high level of unwanted byproducts. Moreover, expensive starting materials, such as (R)-3-aminovaleric acid, were used in this process.

It was found that, in particular, the preparation of the compounds according to formula I was troublesome and expensive.

In order to overcome these problems an improved process for the preparation of the compounds according to formula I was developed by the present inventors. It was surprisingly found that with the so called three-component Povarov reaction compounds according to formula I could be prepared.

The Povarov reaction is a 3-component reaction in which a cis-2-alkyl-4-amino-1,2,3,4-tetrahydroquinoline is formed in one stereoselective step from an aniline, an aldehyde and an enamine (Tetrahedron 2009, 65, 2721). The use of this reaction has been reported in the literature, however its application in the preparation of pharmaceutically active ingredients has been limited due to concerns over storage stability and product purity.

Hence, a first aspect of the present invention relates to a process for preparing the compound of formula I or a salt thereof:

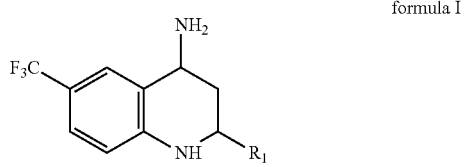

formula I comprising the steps of:
(a) reacting 4-aminobenzotrifluoride according to formula II

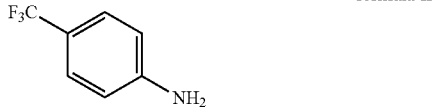

formula II with an aldehyde according to formula III

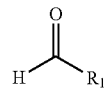

formula III and with a compound according to formula IV

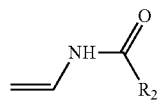

formula IV in the presence of a solvent and optionally one or more catalysts to form the compound of formula V

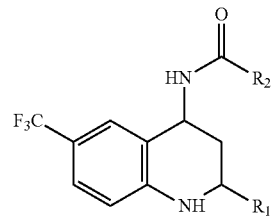

formula V wherein
$R_1$ is H or $C_1$-$C_3$ alkyl, preferably $CH_2CH_3$;
$R_2$ is H, $C_1$-$C_3$ alkyl or

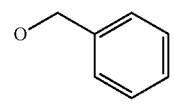

(b) hydrolyzing the compound of formula V to form the compound of formula I.

With the process of the present invention it is now possible to prepare efficiently, with relatively cheap starting materials and with a good yield the compounds according to formula I without many unwanted byproducts.

For the preparation of Compound A it is preferred to use in the process of the present invention compounds wherein $R_1$ is $CH_2CH_3$ and $R_2$ is H. In such as case the aldehyde according to formula III is propionaldehyde and the compound according to formula IV is N-vinylformamide.

After step a) and b) of the present process are carried out, a key intermediate according to formula I is obtained which may be used in the further preparation of tetrahydroquinoline derivatives, such as Compound A.

Since the compounds according to formula I are chiral, it may be desirable to at least partially separate or purify the different enantiomers of the compound of formula I. Such separation or purification is well known in the art and several methods are readily available to the skilled person to execute such a separation or purification.

One preferred way of at least partially separating or purifying the different enantiomers is the use of chiral resolving agents, such as L-tartaric acid or a derivative thereof, such as di-p-toluoyl-L-tartaric acid.

For the preparation of tetrahydroquinoline derivatives having CETP-inhibiting properties, such as Compound A, the use of the 2R,4S enantiomers of the compounds according to formula I are most often needed. Hence, in a further step c) of the process of the present invention the 2R,4S-enantiomer according to formula I-a

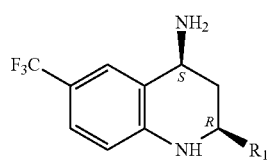

formula I-a is preferably separated from the other stereoisomers.
With respect to the preparation of Compound A it is preferred to separate from the other stereoisomers the compound B (also referred to in WO2007/116922 as (2R,4S)-2-ethyl-6-trifluoromethyl-1,2,3,4-tetrahydroquinolin-4-ylamine)):

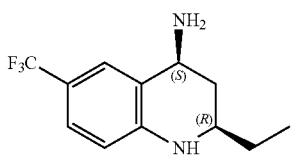

Compound B

Preferably, the separation or purification of the compounds according to formula I is such that the compound according to formula I-a or compound B is obtained with a purity of at least 99% enantiomeric excess (e.e.), preferably at least 99.6% e.e., more preferably at least 99.7% e.e.

After having obtained these compounds they may be reacted into tetrahydroquinoline derivatives having CETP inhibiting properties, such as Compound A, by using the same process as has been described in WO2007/116922.

In one preferred embodiment of the invention, the stoichiometry of the reaction between the aldehyde compound with formula III, the amide compound with formula IV and the 4-aminobenzotrifluoride with formula II ranges from 0.5-5(:)1(:)0.5-1, respectively.

The yield of the compounds according to formula I may also be dependent from the solvent used in step a). Preferably, the solvent used is dichloromethane, acetonitrile, ethyl acetate, toluene or a mixture thereof. If $R_1$ is $CH_2CH_3$ and $R_2$ is H, the reaction of step a) is preferably conducted in dichloromethane, acetonitrile or in a mixture of toluene and dichloromethane.

In a preferred embodiment of the present invention the catalyst used in step a) of the present invention is an acid, preferably a Brønsted acid, or a Lewis acid.

In an even more preferred embodiment according to the invention, the reaction between the aldehyde compound with formula III, the compound with formula IV and the 4-aminobenzotrifluoride with formula II is conducted in the presence of the acid catalyst 4-toluenesulfonic acid. There are a number of addition modes that can successfully result in the desired product. A simultaneous addition mode is preferred so as to prevent formation of difficult to remove product related impurities.

Preferably, in step a) of the process of the present invention a mixture of 4-aminobenzotrifluoride according to formula II and catalyst are added, simultaneously, to the addition of the compound according to formula IV and to the aldehyde according to formula III.

Alternatively, the aldehyde according to formula III, the compound according to formula IV and the 4-aminobenzotrifluoride according to formula II are first mixed in a solvent according to the invention, before contacting the compounds with the catalyst.

Alternatively, the aldehyde according to formula III and the 4-aminobenzotrifluoride according to formula II are first dissolved in a solvent according to the invention, before contacting them with the compound according formula IV and a catalyst according to the invention.

For the purpose of further improving the yield and purity of the compounds according to formula I, the inventors found that it is beneficial to separate the compound of formula V (i.e. the Povarov product) formed in step (a) from the reaction mixture before carrying out the subsequent step (b).

Preferably, the compound of formula V is separated prior to step (b), by means of precipitation and/or filtration procedures. Precipitation of the compound of formula V from the reaction product may be carried out by means of the addition of a non-polar solvent to said reaction mixture. Preferred non-polar solvents are heptanes, cyclohexane or a mixture thereof.

If required, purification is achieved by means of a two-step precipitation process with the compound of formula V. For this purpose, the compound with formula V is preferably in a first step precipitated with heptanes or cyclohexane or a mixture thereof and subsequently recrystallized with acetone, isopropanol, ethyl acetate or methyl tert-butyl ether in a second precipitation step. Further precipitation and/or recrystallization may be carried out to further increase the purity of the compound with formula V.

In step b) of the process of the present invention the compound with formula V is hydrolyzed to form the compound of formula I. Preferably, such hydrolysis is carried out by warming a mixture comprising compound V for 1 to 3 hours at a temperature of 45 to 80° C. in the presence of an aqueous acid, preferably hydrochloric acid.

In a preferred embodiment of the process of the present invention, the compound according to formula V is hydrolyzed in the presence of an alcohol, preferably ethanol, and an aqueous acid.

The compounds according to formula I-a and in particular the compound B are preferably used further in the preparation of tetrahydroquinoline derivatives having CETP inhibiting properties, such as Compound A, by using the same kind of process as has been described in WO2007/116922.

A second aspect of the present invention relates to the compound according to formula V

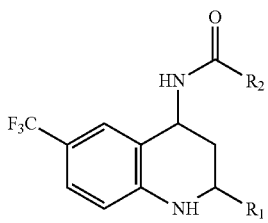

formula V wherein R₂ is H, $C_1$-$C_3$ alkyl or

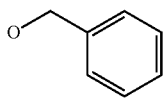

The compound of formula V is the so called Povarov product, which compound has not been synthesized before. The compound according to formula V wherein $R_1$ is $CH_2CH_3$ and $R_2$ is H is particularly preferred for reasons that it is very efficient to use this compound in the preparation of Compound A.

A third aspect of the present invention relates to the use of these compounds in the preparation of a compound according to formula I-a, in particular in the preparation of the compound B.

A last aspect of the present invention relates to the use of a compound of formula V in the preparation of Compound A.

The present invention will be illustrated further by means of the following non-limiting examples.

EXAMPLES

Example 1: Preparation of Racemic cis-N-(2-ethyl-6-(trifluoromethyl)-1,2,3,4-tetrahydroquinolin-4-yl) formamide (Povarov Product)

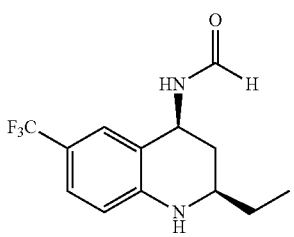 [SMILES: CC[C@@H]1C[C@H](NC=O)c2cc(C(F)(F)F)ccc2N1]

Example 1a) 3 mol % Toluene Sulfonic Acid (TsOH) Catalyzed 3-Component Povarov Reaction Using Simultaneous Addition (50 g Scale)

To a reactor A was added propionaldehyde (90 g, 5 eq) and acetonitrile (50 ml), to a reactor B was added p-toluenesulfonic acid (1.77 g, 3% mol), 4-trifluoromethylaniline (50 g, 1 eq) and acetonitrile (100 ml) and to a reactor C was added N-vinylformamide (26.5 g, 1.2 eq) and acetonitrile (100 mL, 2 vols).

The contents of reactor B and reactor C were added simultaneously to reactor A over ~4 hours whilst keeping the temperature of the contents of reactor A at 20-30° C. After addition, the reaction mixture in reactor A was stirred at 20-25° C. for 16 hours. The mixture was then cooled to 0-5° C. and stirred for 3 hours. The precipitate was filtered off and washed with cold acetonitrile (100 ml). The solid was then dried under vacuum at 40° C. for 16 hours to give 31 g of the Povarov product (37% yield).

Example 1b) 2 mol % p-Toluenesulfonic Acid (TsOH) Catalyzed 3-Component Povarov Reaction in Dichloromethane Overnight (100 g Scale)

4-Aminobenzotrifluoride (100 g, 78 mL, 0.62 mol) was dissolved in $CH_2Cl_2$ (200 mL) at room temperature. Propionaldehyde (44.7 mL, 0.62 mol) was added, followed by $CH_2Cl_2$ (200 mL). The clear solution was stirred at room temperature for 1 hour to give a pale-yellow solution of the imine. The reaction mixture was further diluted with $CH_2Cl_2$ (300 mL) and cooled on ice. N-vinylformamide (86.8 mL, 1.24 mol, 2.0 eq) was added in one portion to the in situ prepared imine solution, as described above. TsOH (2.36 g, 12.4 mmol, 2 mol %) was added to the reaction mixture which was stirred overnight on ice at 0° C. to room temperature. Heptanes (700 mL) were added to the suspension. After 5 minutes the slurry was filtered over a glass filter under suction. The off-white crystals were washed on the filter with heptanes (2×200 mL) under suction. The obtained solids were dried under reduced pressure at 50° C. with a rotary evaporator to give the product (99 g, 59% yield) as an off-white solid. Liquid chromatography-mass spectrometry (LCMS) and ¹H-nuclear magnetic resonance (NMR) confirm the product. Next, the crude solid was recrystallized from hot acetone. Solids that did not dissolve were removed from the hot acetone solution by filtration. The resulting clear solution was stored at 5° C. overnight. The resulting thick slush was filtered using a glass filter and washed with heptanes (2×200 mL). This yielded 52.5 g of a white solid (32% yield). The mother liquor was evaporated and recrystallized from isopropanol (IPA) (+100 mL), yielding 13.5 g of a white solid. Both batches combined gave a yield of 66 g (39% yield). ¹H NMR (300 MHz, $CDCl_3$) δ 8.40 (s, 1H), 7.34 (t, 1H), 7.26 (d, J=7.7 Hz, 1H), 6.52 (d, J=8.4 Hz, 1H), 5.88-5.54 (m, J=26.6 Hz, 1H), 5.52-5.36 (m, 1H), 4.85-4.67 (m, J=16.3, 10.8 Hz, 1H), 4.14 (s, 1H), 3.58-3.31 (m, 1H), 2.45-2.30 (m, 1H), 1.80-1.36 (m, 4H), 1.03 (t, 3H).

Example 2: Preparation of Compound B

Example 2a) Racemic 2-ethyl-6-(trifluoromethyl)-1,2,3,4-tetrahydroquinolin-4-amine (Rac-Compound B)

A mixture of the Povarov product (20 g, 73.5 mmol), concentrated HCl (22.3 mL) and ethanol (60 mL) was heated at 50° C. for 5 hours. After cooling to 30-40° C., the mixture was evaporated to a total volume of 60 ml. The mixture was then cooled and dichloromethane (160 ml) added, followed by basification with 6M NaOH (60 mL) to pH 12-13. The layers were separated and the aqueous phase extracted with dichloromethane (40 mL). The combined organic layers were washed with water (40 mL), dried over sodium sulphate and evaporated to dryness to yield 17.6 g of racemic compound B (95% yield).

Example 2b) Racemic 2-ethyl-6-(trifluoromethyl)-1,2,3,4-tetrahydroquinolin-4-amine (Rac-Compound B) (in Acetonitrile Followed by Sulfuric Acid Hydrolysis)

4-Aminobenzotrifluoride (6.3 mL, 50.0 mmol) was dissolved in $CH_3CN$ (40 mL) at RT. Propionaldehyde (4.3 mL, 60 mmol, 1.2 eq.; stored at 4° C.) was added in one portion. The temperature rose to 25° C. The clear solution was stirred at RT (in a water bath for cooling) for 5 minutes to give a pale-yellow solution of the imine. N-Vinylformamide (4.4 mL, 63 mmol, 1.25 eq.; stored at 4° C.) was added in one portion to the in situ prepared imine solution followed by TsOH (160 mg, 0.017 eq.). The temperature rose to 27° C. After 5 min. a precipitate formed. The mixture was stirred under nitrogen atmosphere at RT overnight. NMR analysis showed full conversion of the components into the Povarov product. To the mixture water (140 mL) was added, followed by $H_2SO_4$ (14 mL) and the mixture was warmed at 60° C. After 0.5 hr NMR revealed full conversion of the Povarov product into the racemic compound B. The mixture was extracted with toluene (50 mL). The aqueous layer was basified with conc. aq. NaOH to pH 10. The basic water layer was extracted with toluene (200 mL) and the toluene layer was dried ($Na_2SO_4$) and concentrated to give 7.3 g (60%) of crude 2-ethyl-6-(trifluoromethyl)-1,2,3,4-tetrahydroquinolin-4-amine (racemic Compound B) as a brown solid, 80-90% pure by NMR. $^1$H NMR (300 MHz, $CDCl_3$) δ 7.62 (s, 1H), 7.28 (d, 1H), 6.45 (d, J=8.4 Hz, 1H), 4.03 (s, 2H), 4.00 (s, 1H), 3.48-3.28 (m, J=2.8 Hz, 1H), 2.27-2.08 (m, 1H), 1.67-1.32 (m, 6H), 1.00 (t, 3H).

Example 2c) Enantiopure (2R,4S)-2-ethyl-6-(trifluoromethyl)-1,2,3,4-tetrahydroquinolin-4-amine (Compound B) by Resolution Di-p-toluoyl-L-tartaric acid monohydrate (134.7 g, 0.33 mol, 0.75 eq) was added to a solution of crude racemic compound B (108.4 g) in methanol (1 L, 9 V) and stirred until crystals formed. The resulting slush was heated to reflux, allowed to cool to RT and then cooled on ice. Crystals formed, which were collected by filtration and dried (99.9 g solids). This material was crystallized again from methanol (750 mL, 7 V) and washed with methyl tert-butyl ether (TBME) (200 mL, 2V) to give 81.6 g compound B ditoluoyltartaric acid (B-DTTA) salt (27% yield) with 99.5% e.e.

Example 2d) Conversion of Compound B Di-p-Toluoyl-L-Tartaric Acid Salt to Methanesulfonic Acid Salt To 10 g compound B-DTTA salt (94% e.e.) was added toluene (100 mL) and 2N NaOH (100 mL). The mixture was stirred for 10 min. after which the layers were separated. The water phase was extracted with toluene (2×100 mL). Next, the combined toluene layers were washed with brine, dried over $Na_2SO_4$ and evaporated to dryness. This resulted in a brown oil, to which 3 V of isopropanol was added. Methanesulfonic acid (MsOH) (1 mL) was added dropwise to the resulting suspension. First the suspension became a clear mixture. After a few min solids started to form. These solids were collected, washed with TBME (2×) and dried. This furnished 4 g (75% yield from enriched compound B-TA salt) of compound B MsOH salt with an e.e. of 98.6%.

10 V of isopropanol (IPA) (40 mL) was added and the resulting suspension was heated to reflux for 5 min. after which it was allowed to cool to RT. Solids formed which were collected by filtration and washed with TBME. This resulted in 2.58 g (48% yield) of compound B MsOH salt with an e.e. of 99.7%.

Example 2e) Conversion of Compound B Methanesulfonic Acid Salt into Compound A

For the conversion of compound B methanesulfonic acid salt into Compound A the similar process as described in WO2007/116922 was used.

Chemical Name and Formula of Compound A

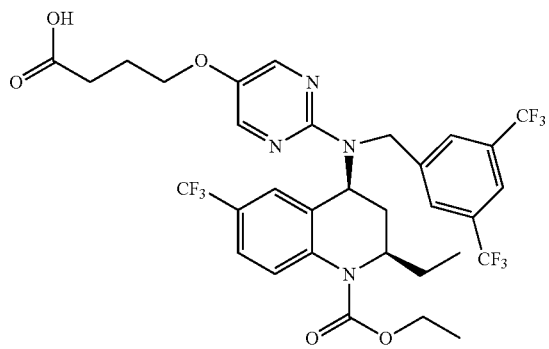 [SMILES: CCOC(=O)N1c2ccc(C(F)(F)F)cc2[C@@H](N(Cc2cc(C(F)(F)F)cc(C(F)(F)F)c2)c2ncc(OCCCC(=O)O)cn2)C[C@H]1CC]

{4-[(2-{[3,5-bis(trifluoromethyl)benzyl] [(2R,4S)-1-(ethoxycarbonyl)-2-ethyl-6-(trifluoromethyl)-1,2,3,4-tetrahydroquinolin-4-yl]amino}pyrimidin-5-yl)oxy]butanoic acid}

REFERENCES

1. The Emerging Risk Factors Collaboration. Major lipids, apolipoproteins, and risk of vascular disease. *JAMA.* 2009; 302:1993-2000.
2. Cholesterol Treatment Trialists (CTT) Collaboration. Efficacy and safety of more intensive lowering of LDL cholesterol: a meta-analysis of data from 170000 participants in 26 randomized trials. *Lancet.* 2010; 13:1670-1681.
3. Roger V L, Go A S, Lloyd-Jones D M et al. Heart disease and stroke statistics—2012 Update: A report from the American Heart Association. *Circulation.* 2012; 125:e12-e230.
4. Barter P J, Caulfield M, Eriksson M et al. Effects of torcetrapib in patients at high risk for coronary events. *N Engl J Med.* 2007; 357:21009-2122.
5. Kastelein J J P, van Leuven S I, Burgess L et al. Effect of torcetrapib on carotid atherosclerosis in familial hypercholesterolemia. *N Engl J Med.* 2007; 356:1620-1630.
6. Nicholls S J, Tuzcu E M, Brennan D M, Tardif J-C, Nissen S E. Cholesteryl ester transfer protein inhibition, high-density lipoprotein raising, and progression of coronary atherosclerosis. Insights from ILLUSTRATE (Investigation of Lipid Level Management Using Coronary Ultrasound to Assess Reduction of Atherosclerosis by CETP Inhibition and HDL Elevation). *Circulation.* 2008; 118:2506-2514.
7. Vergeer M, Bots M L, van Leuven S I, Basart D C, Sijbrands E J, Evans G W, Grobbee D E, Visseren F L, Stalenhoef A F, Stroes E S, Kastelein J J P. Cholesteryl ester transfer protein inhibitor torcetrapib and off-target toxicity: pooled analysis of the rating atherosclerotic disease change by imaging with a new CETP inhibitor (RADIANCE) trials. *Circulation.* 2008; 118:2515-2522.
8. Forrest M J, Bloomfield D, Briscoe R J et al. Torcetrapib-induced blood pressure elevation is independent of CETP inhibition and is accompanied by increasing circulating levels of aldosterone. *Br J Pharmacol.* 2008; 154:1465-1473.
9. Simic B, Hermann M, Shaw S G et al. Torcetrapib impairs endothelial function in hypertension. *Eur Heart J.* 2012; 33:1615-1624.

10. Barter P J, Rye K-A, Beltangady M S et al. Relationship between atorvastatin dose and the harm caused by torcetrapib. *J Lipid Res.* 2012; 53:2436-2442.
11. Schwartz G G, Olsson A G, Abt M et al. Effects of dalcetrapib in patients with recent acute coronary syndrome. *N Engl J Med.* 2012; 367:2089-2099.
12. Stein E A, Stroes E S, Steiner G, et al. Safety and tolerability of dalcetrapib. *Am J Cardiol.* 2009; 104:82-91.
13. Lüscher T F, Taddei S, Kaski J C, et al. Vascular effects and safety of dalcetrapib in patients with or at risk of coronary heart disease: the dal-VESSEL randomized clinical trial. *Eur Heart J.* 2012; 33:857-65.
14. Krishna R, Bergman A J, Fallon et al. Multiple-dose pharmacodynamics and pharmacokinetics of anacetrapib, a potent cholesteryl ester transfer protein (CETP) inhibitor, in healthy subjects. *Clin Pharmacol Ther.* 2008; 84:679-683.
15. Bloomfield D, Carlson G L, Aditi Sapre B S et al. Efficacy and safety of the cholesteryl ester transfer protein inhibitor anacetrapib as monotherapy and coadministered with atorvastatin in dyslipidemic patients. *Am Heart J.* 2009; 157:352-360.
16. Nicholls S J, Brewer H B, Kastelein J J P et al. Effects of the CETP inhibitor evacetrapib administered as monotherapy or in combination with statins on HDL and LDL cholesterol. *JAMA.* 2011; 306:2099-2109.
17. Am. J. Cardiol., 2014 Jan. 1; 113(1):76-83: Evaluation of Lipids, Drug Concentration, and Safety Parameters Following Cessation of Treatment With the Cholesteryl Ester Transfer Protein Inhibitor Anacetrapib in Patients With or at High Risk for Coronary Heart Disease. Antonio M. Gotto Jr. et al.
18. Okamoto M, Sakuragi A, Mori Y, Hamada T, Kubota H, Nakamura Y, Higashijima T, Hayashi N. Tanabe Seiyako Co. Ltd. A process for preparing tetrahydroquinoline derivatives WO 2007/116922 A1.
19. Govindan C K. An improved process for the preparation of benzyl-N-vinyl carbamate. *Org Proc Res Dev.* 2002; 6:74-77.
20. Am Ende D J, DeVries K M, Clifford P J, Brenek S J. A Calorimetric Investigation To Safely Scale-Up a Curtius Rearrangement of Acryloyl Azide *Org Proc Res Dev.* 1998; 2:382-392
21. Damon D B, Dugger R W, Magnus-Aryitey G, Ruggeri R B, Wester R T, Tu M, Abramov Y. Synthesis of the CETP Inhibitor Torcetrapib: The Resolution Route and Origin of Stereoselectivity in the Iminium Ion Cyclization. *Org Proc Res Dev.* 2006; 10:464-471.
22. Liu H, Dagousset G, Masson G, Retailleau P, Zhu J. Chiral Brønsted Acid-Catalyzed Enantioselective Three-Component Povarov Reaction. *J Am Chem Soc.* 2009; 131:4598-4599.
23. Dagousset G, Zhu J, Masson G. Chiral Phosphoric Acid-Catalyzed Enantioselective Three-Component Povarov Reaction Using Enecarbamates as Dienophiles: Highly Diastereo- and Enantioselective Synthesis of Substituted 4-Aminotetrahydroquinolines. *J Am Chem Soc.* 2011; 133:14804-14813.
24. Huang D, Xu F, Chen T, Wang Y, Lin X. Highly enantioselective three-component Povarov reaction catalyzed by SPINOL-phosphoric acids. *RSC Advances.* 2013; 3:573.

The invention claimed is:
1. A process for preparing the racemic compound of formula I or a salt thereof:

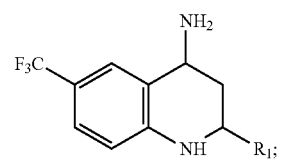

formula I comprising the steps of:
(a) simultaneously reacting 4-aminobenzotrifluoride according to formula II

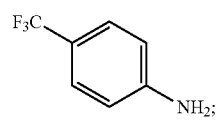

formula II with an aldehyde according to formula III

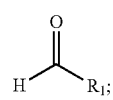

formula III and with a compound according to formula IV

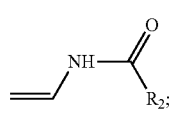

formula IV in the presence of a solvent and optionally one or more catalysts to form the compound of formula V

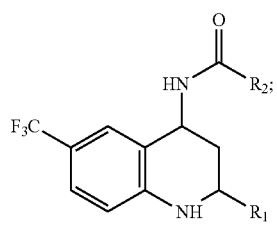

formula V wherein
R₁ is H or C₁-C₃ alkyl;
R₂ is H, C₁-C₃ alkyl or

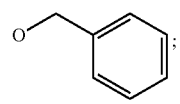

(b) hydrolyzing the compound of formula V to form the compound of formula (I); wherein prior to step (b) the compound of formula V is separated from the reaction mixture of step (a).

2. The process according to claim 1, wherein $R_1$ is $CH_2CH_3$ and $R_2$ is H.

3. The process according to claim 1, wherein the solvent used is dichloromethane, acetonitrile, ethyl acetate, toluene or a mixture thereof.

4. The process according to claim 1, wherein the catalyst used in step a) is an acid, comprising a Brønsted acid or a Lewis acid.

5. The process according to claim 4, wherein the catalyst is 4-toluenesulfonic acid.

6. The process according to claim 1, wherein the compound of formula V is separated from the reaction mixture of step (a) by precipitation from the reaction mixture by means of the addition of a non-polar solvent to said reaction mixture.

7. The process according to claim 6, wherein the non-polar solvent is a heptane, cyclohexane or a mixture thereof.

8. The process according to claim 1, wherein in step (b) the compound of formula V is hydrolyzed by warming a mixture comprising said compound for 1 hour to 3 hours at a temperature of 45° C. to 80° C. in the presence of an aqueous acid or in the presence of an alcohol and an aqueous acid.

9. The process according to claim 8, wherein the acid is hydrochloric acid.

10. The process according to claim 8, wherein the alcohol is ethanol.

11. The process according to claim 1, further comprising a step c) wherein the 2R,4S-enantiomer of the racemic compound of formula I having a molecular formula according to formula I-a

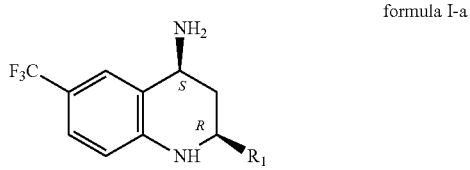

formula I-a wherein, $R_1$ is H or $C_1$-$C_3$ alkyl, is separated from said compound of formula I.

12. The process according to claim 11, wherein the separation of the enantiomer according to formula I-a is carried out by means of resolution with a chiral resolving agent, such as L-tartaric acid or a derivative thereof, such as di-p-toluoyl-L-tartaric acid.

13. The process according to claim 11 wherein $R_1$ $CH_2CH_3$.

14. The process according to claim 12, wherein $R_1$ is $CH_2CH_3$.

15. The process according to claim 11, wherein the compound according to formula I-a is obtained with a purity of at least 99% enantiomeric excess (e.e).

* * * * *